United States Patent
Dick et al.

(10) Patent No.: US 9,180,052 B2
(45) Date of Patent: Nov. 10, 2015

(54) METHOD AND DEVICE FOR NON-INVASIVE TEMPERATURE DETERMINATION IN BIOLOGICAL TISSUE TREATED WITH TREATMENT RADIATION

(75) Inventors: Manfred Dick, Gefell (DE); René Denner, Reisdorf (DE); Stefan Knoke, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 816 days.

(21) Appl. No.: 13/260,176

(22) PCT Filed: Mar. 31, 2010

(86) PCT No.: PCT/EP2010/002048
§ 371 (c)(1),
(2), (4) Date: Dec. 20, 2011

(87) PCT Pub. No.: WO2010/112209
PCT Pub. Date: Oct. 7, 2010

(65) Prior Publication Data
US 2012/0089132 A1    Apr. 12, 2012

(30) Foreign Application Priority Data
Apr. 3, 2009   (DE) .......................... 10 2009 016 184

(51) Int. Cl.
| A61N 5/06 | (2006.01) |
| A61F 9/008 | (2006.01) |
| A61B 5/00 | (2006.01) |
| A61B 5/01 | (2006.01) |
| A61B 17/00 | (2006.01) |
| A61F 9/007 | (2006.01) |

(52) U.S. Cl.
CPC ............... *A61F 9/008* (2013.01); *A61B 5/0095* (2013.01); *A61F 9/00821* (2013.01); *A61B 5/01* (2013.01); *A61B 2017/00084* (2013.01); *A61B 2017/00128* (2013.01); *A61F 9/00727* (2013.01); *A61F 2009/00863* (2013.01)

(58) Field of Classification Search
CPC ..................... A61B 18/20; A61B 2018/00636; A61B 19/5225; A61B 5/4836; A61B 2017/00084; A61B 2017/00128; A61F 9/008
USPC ........................................................ 600/412
See application file for complete search history.

(56) References Cited

U.S. PATENT DOCUMENTS

| 4,741,612 | A | 5/1988 | Birngruber et al. |
| 6,671,043 | B1 | 12/2003 | Huettman |

(Continued)

FOREIGN PATENT DOCUMENTS

| DE | 30 24 169 C2 | 9/1983 |
| DE | 199 16 653 A1 | 10/2000 |
| DE | 199 32 477 A1 | 2/2001 |
| DE | 101 35 944 A1 | 2/2003 |
| DE | 103 01 416 B3 | 7/2004 |

(Continued)

*Primary Examiner* — Aaron Roane
(74) *Attorney, Agent, or Firm* — Petterson Thuente Pedersen, P.A.

(57) ABSTRACT

A method for non-invasive temperature determination in biological tissue treated with treatment radiation wherein a reaction which depends on the treatment temperature is generated and detected. Measurement radiation pulses and pulses of the treatment radiation are applied to the tissue to be treated successively, in particular in an alternating way, from the same radiation source. A device includes a radiation source, an irradiation lens system, detectors for determining a reaction and a system control suitable for controlling treatment radiation and measurement radiation pulses. The system control generates successive, in particular alternating, pulses of treatment radiation and measurement radiation pulses from one radiation source only, in particular a laser which can be modulated.

21 Claims, 2 Drawing Sheets

(56) References Cited

U.S. PATENT DOCUMENTS

| | | |
|---|---|---|
| 6,830,567 B2 | 12/2004 | Schuele et al. |
| 7,357,570 B2 | 4/2008 | Schuele |
| 2002/0173782 A1* | 11/2002 | Cense et al. ............ 606/9 |
| 2005/0206380 A1* | 9/2005 | Seeber ............ 324/315 |
| 2009/0207874 A1 | 8/2009 | Zimare et al. |
| 2010/0292763 A1 | 11/2010 | Brinkmann |

FOREIGN PATENT DOCUMENTS

| | | |
|---|---|---|
| DE | 10 2006 019 127 A1 | 10/2007 |
| EP | 1 279 385 A1 | 1/2003 |
| WO | WO 00 24315 | 5/2000 |
| WO | WO 02/21646 A1 | 3/2002 |
| WO | WO 2004/019774 A1 | 3/2004 |
| WO | WO 2009/056099 A2 | 5/2009 |

* cited by examiner

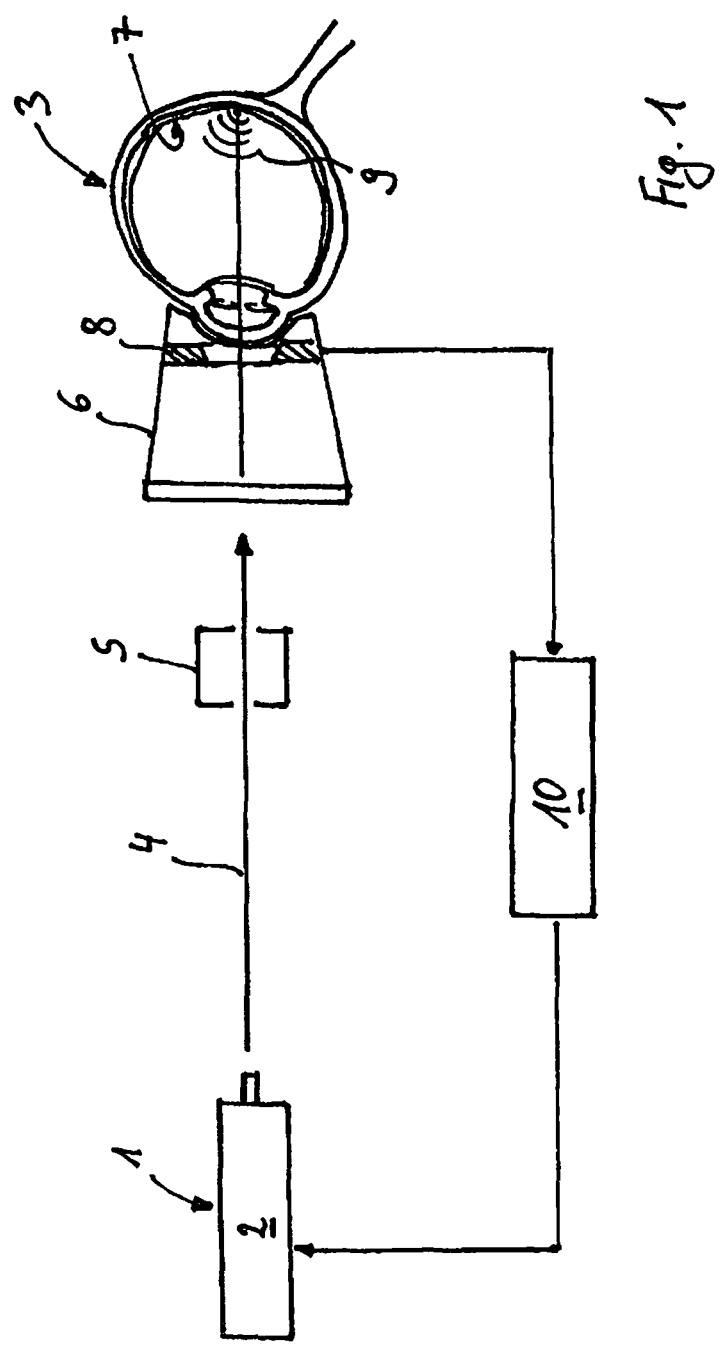

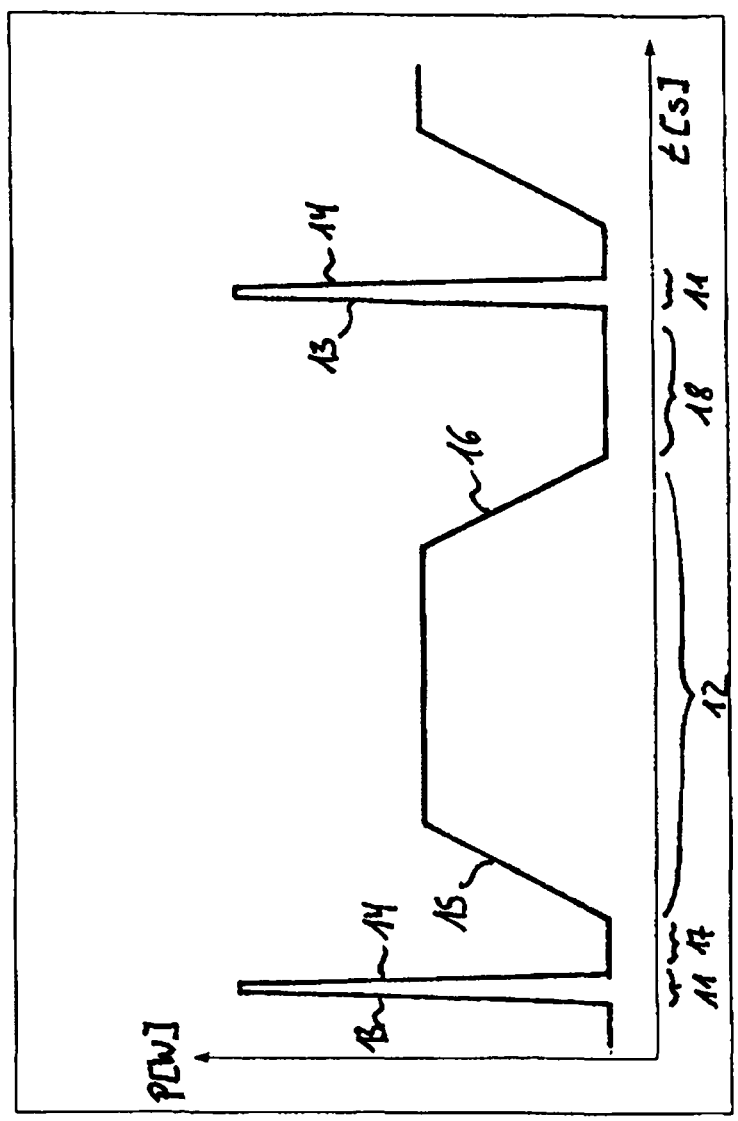

METHOD AND DEVICE FOR NON-INVASIVE TEMPERATURE DETERMINATION IN BIOLOGICAL TISSUE TREATED WITH TREATMENT RADIATION

PRIORITY CLAIM

The present application is a National Phase entry of PCT Application No. PCT/EP2010/002048, filed Mar. 31, 2010, which claims priority from German Application No 102009016184.8, filed Apr. 3, 2009, the disclosures of which are hereby incorporated by reference herein in their entirety.

FIELD OF THE INVENTION

The invention relates to a method for a non-invasive temperature determination on biological tissue treated with a treatment radiation, particularly on a fundus treated by means of laser radiation, wherein a reaction, particularly a pressure wave, which depends on the treatment temperature, is produced by means of measuring radiation pulses and recorded by means of detectors. Furthermore, the invention relates to a device for a non-invasive temperature determination on biological tissue treated with a treatment radiation, particularly on a fundus treated by means of laser radiation, with a radiation source, irradiation optics, detectors for determining a reaction, particularly a pressure wave, as well as a system control suitable for controlling treatment radiation and measuring radiation pulses.

BACKGROUND

The use of high-energy light in ophthalmology, for example, focused sunlight, the radiation of a xenon arc lamp, or from laser beams, e.g., for coagulating retinal tissue on the fundus, is generally known. Thereby, the use of a laser as a radiation source has become particularly important because the spectral wavelength of the laser light can be exactly determined (monochromatic, optionally defined wavelengths in the green, yellow, red, or infrared spectral range) and a precise control of the laser light is possible.

Depending on the type of laser that is used, laser pulses (e.g., with the Nd:YAG laser, wavelength 1064 nm and/or 532 nm—frequency-doubled) or a continuous laser beam (continuous wave=CW laser, e.g., argon laser with wavelengths of blue=488 nm, and green=514 nm, or also the frequency-doubled Nd:YAG laser at 532 nm) are produced. As a rule, argon lasers, dye lasers and solid-state lasers are used for the coagulation of the retina in case of diabetic retinopathy, for peripheral retinal degeneration, for the treatment of retinal holes, as well as for laser trabeculoplasty for decreasing the intraocular pressure. By contrast, $CO_2$ lasers are commonly used for the cutting of tissue.

Temperature control is particularly important for the thermal treatment of tissue. For laser coagulation, irradiation times of 20 ms to 500 ms, particularly approximately 100 ms, are commonly used for creating temperatures above 60° C. Thereby, a laser power of 100 mW to 500 mW is usually applied. With temperatures that are too low, the coagulation effect is insufficient, and with temperatures that are too high, unwanted tissue damage may occur.

A method and a device of the initially stated type, with which a control of the treatment temperature is achieved, are known from the patent document DE 101 35 944 C2. The therein disclosed treatment device exhibits a radiation source in the form of a continuously operating laser (CW laser), the laser beam of which is fed into fiber optics by use of coupling optics, directed towards irradiation optics and from there towards the eye to be treated. Thereby, the laser beam passes through a contact glass which is positioned on the eye and equipped with an acoustic or optical detector.

According to a first embodiment, an additional pulsed radiation source is provided which produces short radiation pulses at predetermined or controlled intervals. Said light pulses exhibit a characteristic which differs from the treatment radiation with regard to pulse duration and energy and are also fed as measuring radiation via the coupling optics to the fiber optics. The pulses of the measuring radiation cause a thermal tissue expansion in the eye, which depends on the temperature caused by the treatment laser and which is evaluable optoacoustically by means of the above-mentioned, e.g., piezoelectric, detectors. Thereby, the thermal expansion caused by the measuring radiation is linearly dependent on the temperature, wherein said dependence can be determined by means of a calibration measurement (Gruneisen coefficient).

According to an alternative suggestion, the additional radiation source is foregone and the treatment beam is instead interrupted for a few nanoseconds. This causes a contraction of the treated tissue on the fundus, the pressure wave of which can also be used for determining the temperature. In this case, a separate measuring beam is not provided.

Reference is expressly made to the embodiments described in the patent document DE 101 35 944 C2 with regard to the basic design and the use of laser radiation in ophthalmology as well as to detectors suitable for recording the expansion.

In the laid-open application DE 199 16 653 A1, a device for individual laser radiation dosage for the transscleral laser cyclophotocoagulation is disclosed, wherein pressure transients are produced in the target tissue of the treatment, with which a treatment plan is made in advance. Furthermore, said information can be utilized in the further course of treatment for the management of the therapy. Thereby, diagnosis pulses with low energy are produced simultaneously with the treatment radiation, which are modulated onto the treatment laser pulse or sent out beforehand. Thereby, the measuring radiation can be sent out beforehand from an additional radiation source or produced through a modulation during the coagulation irradiation with the treatment radiation source.

From the patent document DE 30 24 169 C2, a further method and a further device for operating a photocoagulator for biological tissue, particularly in ophthalmology, is known. Hereby, an arrangement is provided which measures the temporal behavior of the brightness at the point of coagulation, which is caused by the treatment radiation source or a measuring beam which is produced by an additional radiation source. Thereby, the temporal behavior of the brightness during the radiation treatment is utilized for adjusting the exposition parameters.

SUMMARY OF THE INVENTION

The invention addresses the problem of decreasing the equipment expenditure while still allowing for a particularly precise temperature control during the irradiation treatment.

The problem, according to the invention, is solved with regard to the generic method in such a way that measuring radiation pulses and pulses of the treatment radiation are consecutively introduced from the same radiation source in the tissue to be treated. With regard to a device of the initially stated type, the solution provides a system control for producing consecutive pulses of the treatment radiation and the measuring beam pulses from only one radiation source, particularly a modulatable CW laser. Additional internal or external modulators are preferably not utilized.

Preferably, the sequence is designed alternatingly, wherein exactly one pulse of the treatment radiation is provided for exactly one measuring radiation pulse. However, it is basically also conceivable that for controlling the measurement results, two or more measuring radiation pulses follow one another consecutively, or that the pulse of the treatment radiation is interrupted, provided that in the course of the treatment, a pulse of the treatment radiation follows at least one measuring radiation pulse and/or one measuring radiation pulse follows at least one pulse of the treatment radiation.

Producing treatment radiation and measuring radiation pulses by means of only a single radiation source reduces the production costs without decreasing the measurement accuracy. Furthermore, treatment radiation and measuring radiation pulse are both aligned without any further action with the same target volume in the tissue to be treated.

According to an example embodiment of the method, according to the invention, measuring radiation pulses and the pulses of the treatment radiation are produced by a CW laser which, through an appropriate modulation, is particularly suitable for producing radiation pulses of different characteristics, which quickly succeed one another.

The measuring radiation pulse, for example, exhibits a pulse energy of 1 µJ to 20 µJ, in another example preferably greater than 5 µJ, and/or a pulse length of 0.2 µs to 2 µs. As a result, a particularly suitable pressure wave is created for a precise measurement without the measuring radiation pulse significantly contributing to the coagulation of the tissue.

The pulse peak power of the measuring radiation pulse is thereby particularly advantageously 1.5 to 5 times greater than the pulse power of the treatment radiation. Furthermore, a pulse sequence, wherein the pulse length of the treatment radiation is 100 to 1,000 times greater than the pulse length of the measuring radiation pulse, is particularly favorable.

Advantageously, the measuring radiation pulse is produced with a repetition rate of 500 Hz to 10 kHz, for example, smaller than 1 kHz. With repetition rates which are too high, the optically created acoustic waves within the eye and/or the detector would overlap and lead to a distortion or loss of primary information.

A particularly accurate measurement result is achieved when the rising flank of the measuring radiation pulse is set steeper than the rising flank of the pulse of the treatment beam and/or when the falling flank of the measuring radiation pulse is set steeper than the falling flank of the pulse of the treatment beam. Particularly, the time for the rising and/or falling of the measuring beam pulse is for example 0.01 to 0.1 times, in another example approximately 0.05 times, greater than the time for the rising and/or falling of the pulse of the treatment radiation. In addition, it is preferably provided that between the measuring radiation pulse and the following pulse of the treatment radiation, a phase of a complete or particularly incomplete power reduction takes place over a period of 0.5 µs to 100 µs and/or that between the pulse of the treatment radiation and the following measuring radiation pulse a phase of a power reduction takes place over a period of 50 µs to 350 µs.

The modulatable laser, preferably provided for executing the method, according to the invention, and for use in the above-mentioned device, advantageously exhibits an active medium which stores the energy, introduced during the pumping process, for a certain amount of time, e.g., in the form of a population inversion, and emits said energy essentially as single pulse/initial pulse through oscillating the light field in the laser resonator. Solid-state lasers, e.g., exhibit a suitable medium, the energetic storage time of which (also fluorescence lifetime or lifetime in the upper laser level) is usually in the range of 50 µs to 1 ms. A population inversion is present when the population of the energetically higher, upper laser level, which participates in the laser amplification process, is greater than the one of the participating lower laser level.

Preferably, the modulation of the laser is executed in such a way that, at first, a downtime of the laser-pumping source is set, which approximately corresponds to the above-mentioned storage time of the active laser medium, in order to delete the existing radiation field in the laser resonator and to break down a remaining population inversion through spontaneous decay.

Through quick activation of the laser pumping source within approximately 1-10 µs, an excessive buildup of the inversion, due to the lacking radiation field in the resonator, is induced which abruptly breaks down again after the subsequent appearance of a radiation field in the resonator (oscillation process), wherein a short intensive pulse (initial pulse) occurs which reaches pulse durations of approximately 1 µs and power peak values of approximately 10 W (pulse energy 10 µJ) at a maximum CW laser power of the laser of approximately 2 W. The pulses so created are suitable for producing an evaluable optoacoustic signal.

Preferably, the laser pumping power is subsequently temporarily (e.g., for approximately 2 µs) controlled by the following CW power in order to particularly optimize the falling flank of the initial pulse for the optoacoustic effect.

After this modulation cycle and no later than the end of the cycle duration determined through the repetition, the laser pumping source is controlled continuously at the level required for the photocoagulation (e.g., for a laser output power of 2 W) until a new modulation cycle begins. Said control is preferably effected through a control device.

Thereby, the longest possible times for the rising and falling of the coagulation pulse are preferably selected so as to ensure that they do not generate an additional detectable optoacoustic pressure transient. Thereto, the times are for example set in the range of 10 µs-50 µs.

The periodic control of the laser is preferably continued until the switch-off criterion, which is determined by the produced photocoagulation, is reached and the coagulation process is controlledly terminated.

Particularly preferred for the realization of the invention is a diode-pumped solid-state laser, particularly a neodymium yttrium vanadate solid-state laser with a wavelength of 1064 nm and a frequency conversion to the wavelength of 532 nm. Due to the relatively short fluorescence lifetime of the laser-active medium of 100 µs, the switch-off duration for the modulation can be limited to a correspondingly short period of time. For a diode-pumped laser, the radiation pulses can be generated and controlled simply through modulation of the pumping source by means of a suitable interference with the diode current through the system control.

Furthermore, a diode-pumped disc laser, particularly a neodymium yttrium vanadate disc laser with frequency doubling, can advantageously be applied. Due to the design of the laser medium as a very thin disc, which is cooled in axial direction, the buildup of a thermal lens is minimized. This particularly ensures that the radiation parameters do not change at the temporally varying control during the modulation and the coagulation duration; as a result, the advantage of the congruence of measuring and coagulation volume particularly takes effect in accordance with the invention.

For example, diode lasers, YAG lasers, or diode-pumped semiconductor lasers can be further suitable radiation sources. Furthermore, the use of focused light from a xenon lamp, light-emitting diodes (LED), or superluminescent diodes (SLD) is also possible but not necessarily limited to the above.

Basically, multiwavelength laser systems with a plurality of radiation sources, as known, e.g., from DE 10 2006 019 127 A1, are also covered by the claimed invention, provided that one of these radiation sources produces a measuring beam pulse as well as a subsequent pulse of the treatment radiation. Thereby, the remaining radiation sources, e.g., are only used additionally for coagulation and can exhibit the same but also different wavelengths.

BRIEF DESCRIPTION OF THE DRAWINGS

The figures show exemplary and schematically an embodiment of the invention.

FIG. 1 shows a pictorial schematic of the arrangement of a device, according to an example embodiment of the invention;

FIG. 2 shows a diagram of the radiation power for the duration of the execution of a method, according to an example embodiment of the invention;

DETAILED DESCRIPTION

The device shown in FIG. 1 includes a radiation source 1 in the form of a diode-pumped CW laser 2 which produces a laser beam 4, provided for the treatment of an eye 3. Customarily, the laser beam 4 is introduced to the eye 3 by means of not depicted fiber optics and irradiation optics 5 through a contact glass 6 and impinges on the fundus 7.

The contact glass 6 is provided with a detector 8 which records the pressure waves 9, produced through the impinging of the laser beam 4 upon the fundus 7, and which transmits the determined information to the system control 10. In turn, the system control 10 is operatively connected to the radiation source 1.

In applying the method for a non-invasive temperature determination on the fundus 7, which is treated in the embodiment with the laser beam 4, according to the invention, the only radiation source 1 participating in this process is producing measuring radiation pulses 11 and pulses 12 of the treatment radiation in an alternating series, as shown in FIG. 2, which impinge on the same target volume on the fundus 7.

Every measuring beam pulse 11 exhibits a pulse width of approximately 1 µs and a pulse peak power of roughly 10 W at a pulse energy of approximately 10 µJ, wherein a mean power of roughly only 2 W is required for the CW laser. The rising flank 13 and the falling flank 14 of the measuring beam pulse 11 run steeply, resulting in the correspondingly short time for the rising and/or falling of the measuring beam pulse 11.

The times for the rising and/or falling of the pulse 12 of the treatment beam, which follows the measuring beam pulse 11, are considerably longer and preferably lie between 10 µs and 50 µs. Therefore, their duration in the embodiment is approximately 20 times greater than the time for the rising and/or falling of the measuring beam pulse 11. As a result, the rising flank 15 and the falling flank 16 are comparatively flat. This embodiment is particularly advantageous for the coagulation process. In the embodiment, the power of the treatment radiation is at 2 W, wherein the pulse 12 of the treatment beam, if necessary, can be additionally interrupted via the system control 10. For example, a not depicted aperture, which is controlled by the system control, can be used for the interruption.

Between the measuring beam pulse 11 and the temporally following pulse 12 of the treatment radiation, a phase 17 of reduced laser power is provided, during which the CW laser 2 continues to operate at a remaining power (>0 W). Thereby, the laser pumping current is rated such that it exhibits a current intensity >0 A but still lies below the laser threshold of the CW laser 2. A further phase 18 of a corresponding reduction of the laser power is introduced over a somewhat longer period of time between the pulse 12 of the treatment radiation and the temporally following measuring beam pulse 11.

Preferably, this process is repeated with a repetition frequency of 1 kHz (cycle duration 1,000 µs). Thereby, every modulation cycle consists, e.g., of a series of method steps of the following durations:

100 µs Downtime of the pumping source of the CW laser 2 as deletion time of the radiation field; leads to inversion decay;

10 µs Activation of the pumping source (starting oscillation of the measuring beam pulse 11);

1 µs Duration of the measuring beam pulse 11;

20 µs Readjustment time (phase 17) with reduced pumping power;

869 µs Duration of the pulse 12 of the treatment radiation (coagulation duration) with a continuous pumping power for a laser output power of 2 W and times for rising and falling of 50 µs each.

The periodic control of the radiation source 1 is continued until the switch-off criterion, which is determined through the photocoagulation, is reached and the coagulation process is controlledly terminated by the system control 10. In comparison to a temperature-controlled treatment which is not in accordance with the invention, the duration of the coagulation time increases by approximately 10%. However, this additional expenditure of time is overcompensated with the advantage achieved with the invention.

LEGEND

1 Radiation source
2 CW laser
3 Eye
4 Laser beam
5 Irradiation optics
6 Contact glass
7 Fundus
8 Detector
9 Pressure wave
10 System control
11 Measuring radiation pulse
12 Pulse (of the treatment radiation)
13 Flank (of the measuring radiation pulse, rising)
14 Flank (of the measuring radiation pulse, falling)
15 Flank (treatment beam pulse, rising)
16 Flank ((treatment beam pulse, falling)
17, 18 Phase (radiation reduction)
A Ampere
P Power (of the radiation source)
s Second
t Time
W Watt

The invention claimed is:

1. A method for a non-invasive temperature determination on an ocular fundus, that is treated with a treatment radiation, the method comprising;
providing a radiation source that selectively emits measuring radiation pulses and treatment radiation pulses;
providing a detector;

applying the measuring radiation pulses generated by the radiation source to the ocular fundus to produce a reaction that depends on treatment temperature recording the reaction by use of the detector; and applying the measuring radiation pulses and the treatment radiation pulses sequentially to the ocular fundus to be treated from the radiation source.

2. The method, according to claim 1, further comprising applying the treatment radiation as laser radiation.

3. The method, according to claim 1, wherein the reaction that depends on the treatment temperature comprises a pressure wave.

4. The method, according to claim 1, further comprising applying the measuring radiation pulses and the pulses of the treatment radiation alternately.

5. The method, according to claim 1, further comprising producing the measuring radiation pulses and the treatment radiation pulses by application of a modulated continuous wave laser.

6. The method, according to claim 5, further comprising having the modulated continuous wave laser use an alternating initial pulse generation in combination with a temporally dominant continuous wave emission.

7. The method, according to claim 1, further comprising applying the measuring radiation pulse with a pulse energy of 1 µJ to 20 µJ and/or a pulse length of 0.2 µs to 2 µs.

8. The method, according to claim 7, further comprising applying the measuring radiation pulse with a pulse energy greater than 5 µJ.

9. The method, according to claim 7, further comprising applying the measuring radiation pulse with a pulse peak power that is 1.5 to 5 times greater than the peak power of the pulse of the treatment radiation.

10. The method, according to claim 9, further comprising applying the treatment beam with the length of the pulse of the treatment beam 100 to 1,000 times greater than the pulse length of the measuring radiation pulse.

11. The method, according to claim 7, further comprising applying the treatment beam with the length of the pulse of the treatment beam 100 to 1,000 times greater than the pulse length of the measuring radiation pulse.

12. The method, according to claim 1, further comprising producing the measuring radiation pulse with a repetition rate of 500 Hz to 10 kHz.

13. The method, according to claim 12, further comprising producing the measuring radiation pulse with the repetition rate smaller than 1 kHz.

14. The method, according to claim 1, further comprising delivering laser radiation such that a rising flank of the measuring radiation pulse is set steeper than a rising flank of the pulse of the treatment beam.

15. The method, according to claim 14, further comprising delivering laser radiation such that a time for the rising and/or falling of the measuring beam pulse is approximately 0.01 to 0.1 times, greater than a time for the rising and/or falling of the pulse of the treatment radiation.

16. The method, according to claim 14, further comprising delivering laser radiation such that a time for the rising and/or falling of the measuring beam pulse is approximately 0.05 times, greater than a time for the rising and/or falling of the pulse of the treatment radiation.

17. The method, according to claim 1, further comprising delivering laser radiation such that a falling flank of the measuring radiation pulse is set steeper than a falling flank of the pulse of the treatment beam.

18. The method, according to claim 17, further comprising delivering laser radiation such that a time for the rising and/or falling of the measuring beam pulse is approximately 0.01 to 0.1 times greater than a time for the rising and/or falling of the pulse of the treatment radiation.

19. The method, according to claim 17, further comprising delivering laser radiation such that a time for the rising and/or falling of the measuring beam pulse is approximately 0.05 times, greater than a time for the rising and/or falling of the pulse of the treatment radiation.

20. The method according to claim 1, further comprising delivering laser radiation such that between the measuring radiation pulse and a following pulse of the treatment radiation, a phase of a power reduction takes place over a period of 0.5 µs to 100 µs.

21. The method according to claim 1, further comprising delivering laser radiation such that between the pulse of the treatment radiation and a following measuring radiation pulse, a phase of a power reduction takes place over a period of 50 µs to 350 µs.

* * * * *